United States Patent [19]

Cheng et al.

[11] Patent Number: 5,493,065
[45] Date of Patent: Feb. 20, 1996

[54] LIQUID PHASE ETHYLBENZENE SYNTHESIS WITH MCM-49

[75] Inventors: Jane C. Cheng, Clarksburg; C. Morris Smith, Princeton, both of N.J.; Dennis E. Walsh, Richboro, Pa.

[73] Assignee: Mobil Oil Corp., Fairfax, Va.

[21] Appl. No.: 319,318

[22] Filed: Oct. 6, 1994

Related U.S. Application Data

[63] Continuation of Ser. No. 78,368, Jun. 16, 1993, abandoned.

[51] Int. Cl.⁶ .................................................. C07C 2/66
[52] U.S. Cl. ................................. 585/467; 585/446
[58] Field of Search ................................. 585/467, 446

[56] References Cited

U.S. PATENT DOCUMENTS

| | | | |
|---|---|---|---|
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 4,954,663 | 9/1990 | Marler et al. | 568/791 |
| 4,962,256 | 10/1990 | Le et al. | 585/467 |
| 4,981,663 | 1/1991 | Rubin | 423/277 |
| 4,992,606 | 2/1991 | Kushnerick et al. | 585/467 |
| 5,001,295 | 3/1991 | Angevine et al. | 585/467 |
| 5,021,141 | 6/1991 | Rubin | 208/46 |
| 5,043,501 | 8/1991 | Del Rossi et al. | 585/323 |
| 5,077,445 | 12/1991 | Le | 585/467 |
| 5,149,894 | 9/1992 | Holtermann et al. | 585/467 |
| 5,334,795 | 8/1994 | Chu et al. | 585/467 |

FOREIGN PATENT DOCUMENTS 0293032  11/1988  European Pat. Off. .

*Primary Examiner*—Anthony McFarlane
*Attorney, Agent, or Firm*—Alexander J. McKillop; Dennis P. Santini; Edward F. Kenehan, Jr.

[57] ABSTRACT

There is provided a process for the liquid phase synthesis of ethylbenzene with a zeolite designated MCM-49. The process involves the alkylation of benzene with ethylene under liquid phase conditions.

5 Claims, 2 Drawing Sheets

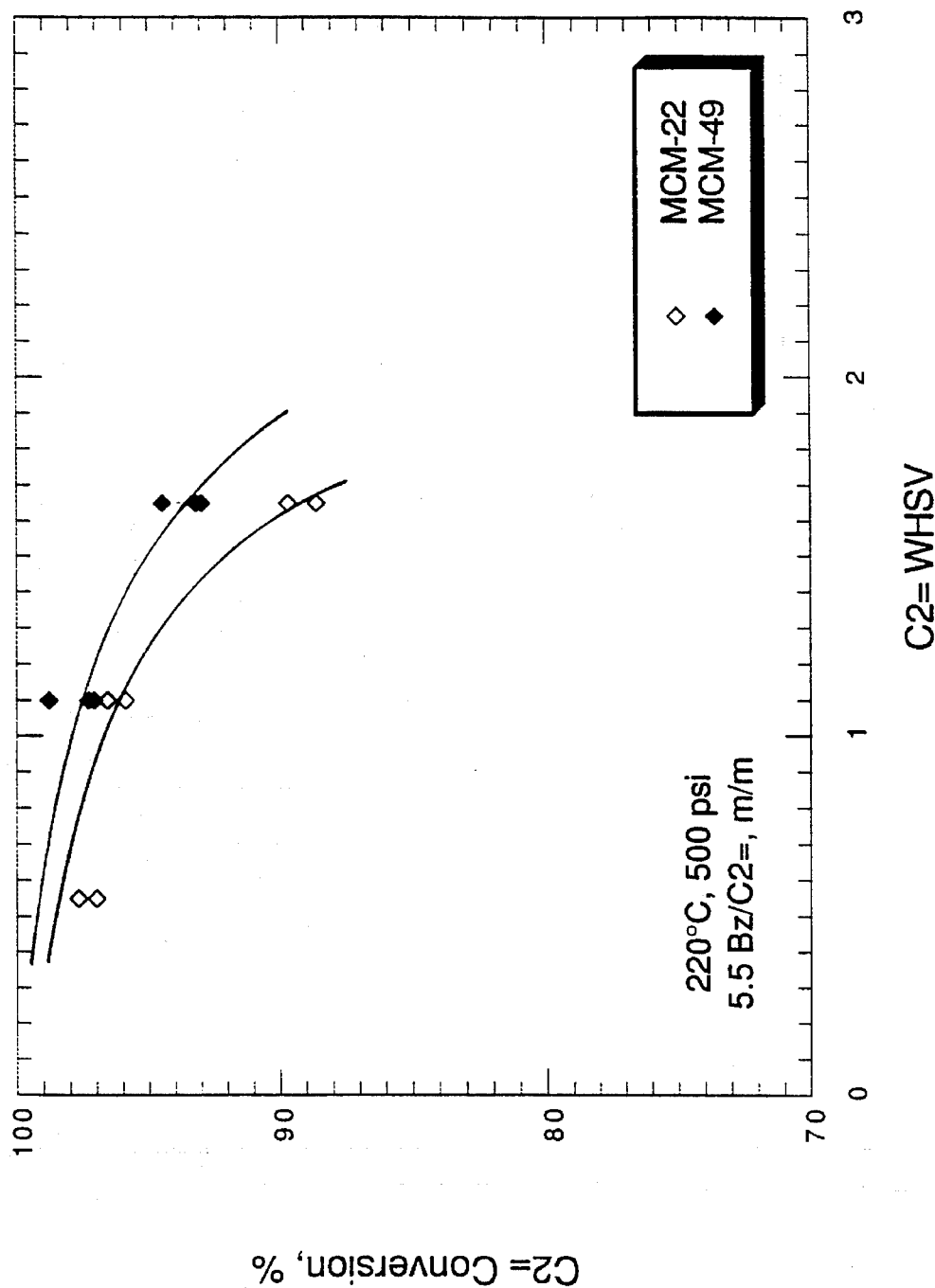
Figure 1. Comparison of Activity

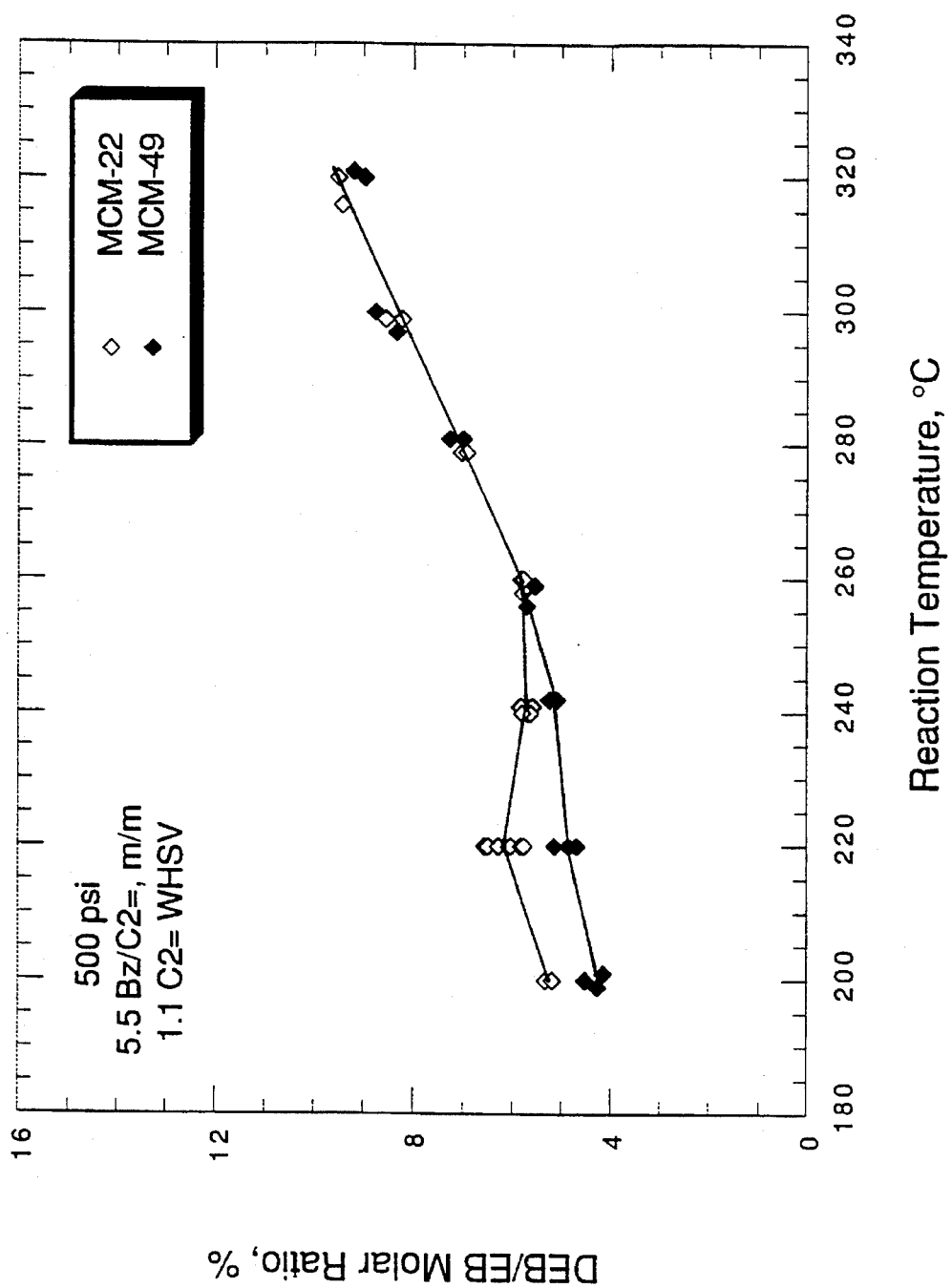

LIQUID PHASE ETHYLBENZENE SYNTHESIS WITH MCM-49

CROSS-REFERENCE TO RELATED APPLICATION

This application is a continuation of copending U.S. application Ser. No. 08/078,368, filed Jun. 16, 1993, now abandoned.

BACKGROUND

There is provided a process for the liquid phase synthesis of ethylbenzene with a zeolite designated MCM-49.

Ethylbenzene is a valuable commodity chemical which is currently used on a large scale industrially for the production of styrene monomer. Ethylbenzene may be produced by a number of different chemical processes but one process which has achieved a significant degree of commercial success is the vapor phase alkylation of benzene with ethylene in the presence of a solid, acidic ZSM-5 zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° to 900° F. (315° to 480° C.), but are usually maintained above about 700° F. (about 370° C.) in order to keep the content of the more highly alkylated benzenes such as diethylbenzene at an acceptably low level. Pressures typically vary from atmospheric to 3000 psig (about 20785 kPa abs) with a molar ratio of benzene to ethylene from about 1:1 to 25:1, usually about 5:1 (benzene:ethylene). Space velocity in the reaction is high, usually in the range of 1 to 6, typically 2 to 5, WHSV based on the ethylene flow, with the benzene space velocity varying accordingly, in proportion to the ratio of the reactants. The products of the reaction include ethylbenzene which is obtained in increasing proportions as temperature increases together with various polyethylbenzenes, principally diethylbenzene (DIEB) which also are produced in increasing amounts as reaction temperature increases. Under favorable operating conditions on the industrial scale, an ethylene conversion in excess of 99.8 weight percent may be obtained at the start of the cycle.

In a commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level. This commercial process is known as the Mobil/Badger process and is described in more detail in an article by Francis G. Dwyer, entitled "Mobil/Badger Ethylbenzene Process-Chemistry and Catalytic Implications" appearing on pages 39–50 of a book entitled *Catalysis of Organic Reactions*, edited by William R. Moser, Marcel Dekker, Inc., 1981.

Ethylbenzene production processes are described in U.S. Pat. Nos. 3,751,504 (Keown), 4,547,605 (Kresge), and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pats. Nos. 4,169,11 (Wight) and 4,459,426 (Inwood), in both of which a preference for large pore size zeolites such as zeolite Y is expressed, in distinction to the intermediate pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

Ethylbenzene (EB) can be synthesized from benzene and ethylene ($C_2=$) over a variety of zeolitic catalysts in either the liquid phase or in the vapor phase. An advantage of a liquid phase process is its low operating temperature and the resulting low content of by-products.

U.S. Pat. No. 4,891,458 describes the liquid phase synthesis of ethylbenzene with zeolite beta.

U.S. Pat. No. 5,149,894 describes the liquid phase synthesis of ethylbenzene with a crystalline aluminosilicate material designated SSZ-25.

Copending U.S. application Ser. No. 07/967,954, filed Oct. 27, 1992, now U.S. Pat. No. 5,334,795, describes the liquid phase synthesis of ethylbenzene with a crystalline aluminosilicate material designated MCM-22.

SUMMARY

There is provided a process for the production of ethylbenzene, said process comprising alkylating benzene with ethylene under sufficient liquid phase conditions in the presence of a catalyst comprising MCM-49, said MCM-49 having, in as-synthesized form, the X-ray diffraction pattern of Table 1, and said MCM-49 having, in calcined form, the X-ray diffraction pattern of Table 2, wherein the form of the MCM-49 in said catalyst is a calcined, aluminosilicate form.

BRIEF DESCRIPTION OF THE DRAWINGS

FIG. 1 is a graph showing a comparison of the activities of MCM-49 and MCM-22 in the liquid phase synthesis of ethylbenzene.

FIG. 2 is a graph showing a comparison of the selectivities of MCM-49 and MCM-22 in the liquid phase synthesis of ethylbenzene.

EMBODIMENTS

The catalyst in the present liquid phase alkylation reaction comprises a crystalline material designated MCM-49. MCM-49 and methods for its preparation are described in copending U.S. application Ser. No. 07/802,938, filed Dec. 6, 1991, now U.S. Pat. No. 5,236,575, the entire disclosure of which is expressly incorporated herein by reference.

MCM-49 may exist in a number of forms depending, for example, upon its composition and thermal history. A particular form of MCM-49, based upon composition, is the aluminosilicate form, wherein the framework of the MCM-49 crystal structure consists essentially of silica and alumina. Forms of MCM-49, based upon thermal history, include the as-synthesized form and the calcined form.

These as-synthesized and calcined forms of MCM-49 are described more particularly hereinafter.

MCM-49 has been discovered to be active and very selective for liquid phase ethylbenzene synthesis. This selectivity advantage could be translated to a lower benzene recycle ratio and lower down stream separation costs while maintaining product quality.

In the as-synthesized form, MCM-49 appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table 1 below:

TABLE 1

| Interplanar d-Spacing (Å) | Relative Intensity, I/Io × 100 |
|---|---|
| 13.15 ± 0.26 | w–s* |
| 12.49 ± 0.24 | vs |
| 11.19 ± 0.22 | m–s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

In its calcined form, MCM-49 transforms to a single crystal phase with little or no detectable impurity crystal phases having an X-ray diffraction pattern which is not readily distinguished from that of MCM-22, but distinguishable from the patterns of other known crystalline materials. The X-ray diffraction pattern of the calcined form of MCM-49 includes the lines listed in Table 2 below:

TABLE 2

| Interplanar d-Spacing (Å) | Relative Intensity, I/Io × 100 |
|---|---|
| 12.41 ± 0.24 | vs |
| 11.10 ± 0.22 | s |
| 8.89 ± 0.17 | m–s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w–m |
| 3.92 ± 0.08 | w–m |
| 3.75 ± 0.07 | w–m |
| 3.57 ± 0.07 | w |
| 3.43 ± 0.07 | s–vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

MCM-49, in its calcined form, may have a bulk silica:alumina ($SiO_2$:$Al_2O_3$) molar ratio of less than about 24:1, preferably less than about 20:1.

MCM-49 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, hexamethyleneimine directing agent (R), and water, said reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/x_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum is present, the $YO_2/Al_2O_3$ ratio must be less than about 35.

The source of $YO_2$ may be soluble or insoluble, but is preferably comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound and $H_2O$ of hydration and having a particle size of about 0.02 micron) favors crystalline MCM-49 formation from the above mixture. Preferably, therefore, the solid $YO_2$, e.g., silica, source contains at least about 30 wt. % solid $YO_2$, e.g., silica, and more preferably at least about 40 wt. % solid $YO_2$, e.g., silica.

Crystallization of MCM-49 can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of MCM-49 may be facilitated by the presence of at least 0.01 percent, preferably 0.10 percent and still more preferably 1 percent, seed crystals (based on total weight) of crystalline product. Useful seed crystals include MCM-22 and/or MCM-49.

Directing agent R for making MCM-22 or MCM-49 may be selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

The MCM-49 crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the process of this invention. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the MCM-49, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The alkylation reaction is carried out in the liquid phase. Suitable conditions can be selected by reference to the phase diagram for benzene.

In the liquid phase, the reaction is carried out with the benzene feedstock in the liquid phase with the reaction conditions (temperature, pressure) appropriate to this end.

Liquid phase operation may be carried out at temperatures between 300° and 500° F. (about 150° to 260° C.), usually in the range of 400° to 500° F. (about 205° to 260° C.).

Pressures during the alkylation step may be as high as about 3000 psig, (about 20875 kPa abs.) and generally will not exceed 1000 psig (about 7000 kPa). The reaction may be carried out in the absence of hydrogen and accordingly the prevailing pressures are those of the reactant species. In a high pressure liquid phase operation, the temperature may be from about 300° to 600° F. with the pressure in the range of about 400 to 800 psig. The space velocity may be from about 0.1 to 10 WHSV, based on the ethylene feed, although lower space velocities are preferred for the liquid phase reaction, for example, from about 0.1 to about 1 WHSV with values from about 0.2 to 0.5 WHSV (ethylene) being typical. The ratio of the benzene to the ethylene in the alkylation reactor may be from 1:1 to 30:1 molar (benzene:ethylene, fresh feed) normally about 5:1 to 20:1 and in most cases from about 5:1 to 10:1 molar.

The alkylation process can be carried out as a batch-type, semi-continuous or continuous operation utilizing a fixed, fluidized or moving bed catalyst system.

EXAMPLE 1

A 2.24 part quantity of 45% sodium aluminate was added to a solution containing 1.0 part of 50% NaOH solution and 43.0 parts $H_2O$ in an autoclave. An 8.57 part quantity of Ultrasil precipitated silica was added with agitation, followed by 4.51 parts of HMI.

The reaction mixture had the following composition, in mole ratios:

| | |
|---|---|
| $SiO_2/Al_2O_3 =$ | 23 |
| $OH^-/SiO_2 =$ | 0.21 |
| $Na/SiO_2 =$ | 0.21 |
| $HMI/SiO_2 =$ | 0.35 |
| $H_2O/SiO_2 =$ | 19.3 |

The mixture was crystallized at 150° C. for 84 hours with stirring. The product was identified as MCM-49 and had the X-ray pattern which appears in Table 3.

The chemical composition of the product was, in wt. %:

| | |
|---|---|
| N | 1.70 |
| Na | 0.70 |
| $Al_2O_3$ | 7.3 |
| $SiO_2$ | 74.5 |
| Ash | 84.2 |

The silica/alumina mole ratio of the product was 17.3.

The sorption capacities, after calcining at 538° C. for 9 hours were, in wt. %:

| | |
|---|---|
| Cyclohexane, 40 Torr | 10.0 |
| n-Hexane, 40 Torr | 13.1 |
| $H_2O$, 12 Torr | 15.4 |

A portion of the sample was calcined in air for 3 hours at 8° C. This material exhibited the X-ray diffraction pattern shown in Table 4.

TABLE 3

| Degrees 2-Theta | Interplanar d-spacing (A) | $I/I_o$ |
|---|---|---|
| 3.1 | 28.5 | 18 |
| 3.9 | 22.8 | 7+ |
| 6.81 | 12.99 | 61 sh |
| 7.04 | 12.55 | 97 |
| 7.89 | 11.21 | 41 |
| 9.80 | 9.03 | 40 |
| 12.76 | 6.94 | 17 |
| 13.42 | 6.60 | 4* |
| 13.92 | 6.36 | 17 |
| 14.22 | 6.23 | 11 |
| 14.63 | 6.05 | 2 |
| 15.81 | 5.61 | 15 |
| 17.71 | 5.01 | 4 |
| 18.86 | 4.71 | 4 |
| 19.23 | 4.62 | 6 |
| 20.09 | 4.42 | 27 |
| 20.93 | 4.24 | 8 |
| 21.44 | 4.14 | 17 |
| 21.74 | 4.09 | 37 |
| 22.16 | 4.01 | 17 |
| 22.56 | 3.94 | 58 |
| 23.53 | 3.78 | 26 |
| 24.83 | 3.59 | 22 |
| 25.08 | 3.55 | 10 |
| 25.86 | 3.45 | 100 |
| 26.80 | 3.33 | 28 |
| 27.53 | 3.24 | 21 |
| 28.33 | 3.15 | 15 |
| 28.98 | 3.08 | 4 |
| 29.47 | 3.03 | 2 |
| 31.46 | 2.843 | 4 |
| 32.08 | 2.790 | 6 |
| 33.19 | 2.699 | 9 |
| 34.05 | 2.633 | 5 |

TABLE 3-continued

| Degrees 2-Theta | Interplanar d-spacing (A) | I/I$_o$ |
|---|---|---|
| 34.77 | 2.580 | 4 |
| 36.21 | 2.481 | 2 |
| 36.90 | 2.436 | 3 |
| 37.68 | 2.387 | 8 | sh = Shoulder
+ = Non-crystallographic MCM-49 peak
* = Impurity peak

TABLE 4

| Degrees 2-Theta | Interplanar d-spacing (A) | I/I$_o$ |
|---|---|---|
| 3.2 | 28.0 | 9+ |
| 3.9 | 22.8 | 7+ |
| 6.90 | 12.81 | 48 sh |
| 7.13 | 12.39 | 100 |
| 7.98 | 11.08 | 46 |
| 9.95 | 8.89 | 53 |
| 12.87 | 6.88 | 10 |
| 14.32 | 6.18 | 36 |
| 14.74 | 6.01 | 11 |
| 15.94 | 5.56 | 17 |
| 17.87 | 4.96 | 2 |
| 19.00 | 4.67 | 5 |
| 19.35 | 4.59 | 3 |
| 20.24 | 4.39 | 14 |
| 21.06 | 4.22 | 5 |
| 21.56 | 4.12 | 15 |
| 21.87 | 4.06 | 25 |
| 22.32 | 3.98 | 12 |
| 22.69 | 3.92 | 41 |
| 23.69 | 3.76 | 23 |
| 24.95 | 3.57 | 19 |
| 25.22 | 3.53 | 4 |
| 25.99 | 3.43 | 90 |
| 26.94 | 3.31 | 20 |
| 27.73 | 3.22 | 17 |
| 28.55 | 3.13 | 11 |
| 29.11 | 3.07 | 3 |
| 29.63 | 3.01 | 2 |
| 31.59 | 2.833 | 6 |
| 32.23 | 2.777 | 4 |
| 33.34 | 2.687 | 9 |
| 34.35 | 2.611 | 4 |
| 34.92 | 2.570 | 3 |
| 36.35 | 2.471 | 2 |
| 37.07 | 2.425 | 2 |
| 37.82 | 2.379 | 6 | sh = Shoulder
+ = Non-crystallographic MCM-49 peak

EXAMPLE 2

The calcined portion of the product of Example 1 was ammonium exchanged and calcined at 538° C. in air for 3 hours to provide the hydrogen form transformation product of the crystalline MCM-49. The Alpha Test proved this material to have an Alpha Value of 308.

EXAMPLE 3

Sodium aluminate comprising 40 wt. % Al$_2$O$_3$, 33 wt. % Na$_2$O, and 27 wt. % H$_2$O was added to a solution containing NaOH and H$_2$O in an autoclave. Ultrasil precipitated silica was then added with agitation, followed by aminocycloheptane (R) directing agent to form a reaction mixture.

This mixture had the following composition, in mole ratios:

| | |
|---|---|
| SiO$_2$/Al$_2$O$_3$ = | 33.3 |
| OH$^-$/SiO$_2$ = | 0.18 |
| Na/SiO$_2$ = | 0.18 |
| R/SiO$_2$ = | 0.35 |
| H$_2$O/SiO$_2$ = | 18.8 |

The mixture was crystallized at 143° C. for 192 hours with stirring. The product was identified as MCM-49 and had the X-ray pattern which appears in Table 5.

The chemical composition of the product was, in wt. %:

| | |
|---|---|
| N | 1.51 |
| Na | 0.83 |
| Al$_2$O$_3$ | 4.6 |
| SiO$_2$ | 74.2 |
| Ash | 79.2 |

The silica/alumina mole ratio of the product was 27.4.

The sorption capacities, after calcining at 538° C. for 9 hours were, in wt. %:

| | |
|---|---|
| Cyclohexane, 40 Torr | 7.5 |
| n-Hexane, 40 Torr | 14.0 |
| H$_2$O, 12 Torr | 13.5 |

TABLE 5

| Degrees 2-Theta | Interplanar d-spacing (A) | I/I$_o$ |
|---|---|---|
| 4.1 | 21.4 | 1 |
| 6.87 | 12.87 | 41 |
| 7.14 | 12.38 | 100 |
| 7.98 | 11.09 | 26 |
| 9.88 | 8.95 | 18 |
| 12.85 | 6.89 | 14 |
| 14.00 | 6.33 | 10 |
| 14.31 | 6.19 | 11 |
| 14.74 | 6.01 | 2 |
| 15.88 | 5.58 | 13 |
| 17.79 | 4.99 | 4 |
| 18.95 | 4.68 | 6 |
| 19.34 | 4.59 | 7 |
| 20.20 | 4.40 | 18 |
| 21.06 | 4.22 | 7 |
| 21.51 | 4.13 | 12 |
| 21.82 | 4.07 | 27 |
| 22.63 | 3.93 | 46 |
| 23.60 | 3.77 | 19 |
| 24.90 | 3.58 | 25 |
| 25.14 | 3.54 | 7 |
| 25.92 | 3.44 | 90 |
| 26.82 | 3.32 | 26 |
| 27.66 | 3.22 | 13 |
| 28.43 | 3.14 | 12 |
| 29.03 | 3.08 | 4 |
| 29.45 | 3.03 | 3 |
| 31.51 | 2.839 | 4 |
| 32.15 | 2.784 | 5 |
| 33.24 | 2.695 | 8 |
| 34.13 | 2.627 | 4 |
| 34.84 | 2.575 | 2 |
| 36.26 | 2.477 | 3 |
| 36.97 | 2.431 | 3 |
| 37.73 | 2.384 | 7 |

EXAMPLE 4

For comparison purposes, Example 1 of U.S. Pat. No. 4,954,325, incorporated herein by reference, was repeated. The as-synthesized crystalline material of the Example, referred to herein as MCM-22 precursor or the precursor form of MCM-22, was examined by X-ray diffraction analysis. Its X-ray diffraction pattern is presented in Table 6. The X-ray diffraction pattern of the calcined form of this material (538° C. for 20 hours) is shown in Table 7 below, and in FIG. 1 of U.S. Pat. No. 4,954,325.

TABLE 6

| Degrees 2-Theta | Interplanar d-spacing (A) | I/I$_o$ |
| --- | --- | --- |
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

TABLE 7

| Degrees 2-Theta | Interplanar d-spacing (A) | I/I$_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 19.08 | 4.65 | 2 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 25.01 | 3.56 | 20 |
| 26.00 | 3.43 | 100 |
| 26.96 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 5

In order to provide a catalyst for comparative testing, a catalyst comprising MCM-22 was prepared as described hereinafter.

1.71 parts of 45% sodium aluminate solution were added to a solution containing 1.0 parts of 50% NaOH solution and 43.0 parts of H$_2$O in an autoclave. 8.57 parts of Ultrasil precipitated silica were added with agitation, followed by 4.51 parts of HMI.

The reaction mixture had the following composition, in mole ratios:

| | |
| --- | --- |
| SiO$_2$/Al$_2$O$_3$ | 30 |
| OH$^-$/SiO$_2$ | 0.18 |
| R/SiO$_2$ | 0.35 |
| H$_2$O/SiO$_2$ | 19.4 |

The mixture was crystallized at 149° for 78 hours with stirring. The chemical composition of the product was, in wt. %:

| | |
| --- | --- |
| N | 1.80 |
| Na | 0.50 |
| Al$_2$O$_3$ | 5.5 |
| SiO$_2$ | 76.2 |
| Ash | 80.5 |
| SiO$_2$/Al$_2$O$_3$, mole ratio | 23.5/1 |

The sorption capacities, after calcining at 538° C. for 6 hours were, in wt. %:

| | |
| --- | --- |
| Cyclohexane, 40 Torr | 12.6 |
| N-Hexane, 40 Torr | 9.3 |
| H$_2$O, 12 Torr | 15.3 |

A portion of the uncalcined MCM-22 precursor drycake was mixed with alumina (Davison VFA) in proportions to give 65% MCM-22/35% alumina on a 100% solids basis. Deionized (DI) water was added to give an extrudable mull and the mix extruded to 1/16 inch diameter and dried at 120° C. The dried extrudate was calcined in flowing nitrogen at 482° C. for 3 hours. It was then charged to a column and exchanged 2 times for 1 hour with 1N NH$_4$NO$_3$ solution (5 ml solution per gram of extrudate) at room temperature, washed with DI water, and dried at 120° C. The extrudate was then calcined in flowing air at 538° C. for 6 hours.

EXAMPLE 6

A catalyst comprising MCM-49 was prepared as described hereinafter.

A portion of the uncalcined MCM-49 precursor drycake as prepared in Example 1 was mixed with alumina (LaRoche Versal 250) in proportions to give 65% MCM-49/35% alumina on a 100% solids basis. DI water was added to give an extrudable mull and the mix was extruded to 1/16 inch diameter and dried at 120° C. The dried extrudate was calcined in flowing nitrogen at 482° C. for 6 hours. It was then charged to a column and exchanged 3 times for 1 hour with 1N NH$_4$NO$_3$ solution (5 ml solution per gram of extrudate) at room temperature, washed with DI water, and dried at 120° C. The extrudate was heated in flowing nitrogen to 482° C., the atmosphere switched to flowing air, the temperature raised to 538° C., and finally calcined in flowing air for 12 hours at 538° C.

EXAMPLE 7

The catalysts of Examples 5 and 6 were evaluated for the liquid phase alkylation of benzene with ethylene. More particularly, a three-zone isothermal fixed-bed unit was used to evaluate the catalysts comprising MCM-49 and MCM-22. Two grams of each catalyst (1/16 " diameter×1/16 " length)

were diluted to ~20 cc with 20–40 mesh vycor chips to make up the active bed. Benzene was fed as liquid while $C_2^=$ was fed as gas to the top of the reactor. The reactor was operated at 500 psi, 4.5–7.5 benzene/$C_2^=$ molar ratio, 0.55–3.3 $C_2^=$ WHSV, and 160°–320° C. Offgases were analyzed on a Carle refinery gas analyzer and liquid products were analyzed on a Varian 3700 GC equipped with an SPB-5 capillary column. Ethylene conversion was determined by measuring unreacted $C_2^=$ offgas relative to feed $C_2^=$. Total material balances were 100±2%.

The activity of the catalysts, measured at 220° C., 500 psi, and 5.5 benzene/$C_2^=$ molar ratio, are compared in FIG. 1. At constant C2= conversion, the $C_2^=$ WHSV with MCM-49 is slightly higher than that with MCM-22, i.e., MCM-49 is slightly more active than MCM-22.

The selectivity of the catalysts is compared in the following table.

| Catalyst | MCM-22 | MCM-49 |
|---|---|---|
| Product dist. (mol %) | | |
| EB | 94.0 | 95.3 |
| DEB | 5.7 | 4.5 |
| TEB | 0.2 | 0.1 |
| Σ | 99.9 | 99.9 |
| xylenes | 0.00 | 0.00 |
| n-$C_3$-Bz/cumene | 0.00 | 0.00 |
| sec-$C_4$-Bz | 0.07 | 0.06 |
| other $C_9$+ aromatics | 0.02 | 0.02 |
| Σ (by products) | 0.09 | 0.08 |

97% $C_2$ = conversion at 220° C., 500 psi, and 5.5 benzene/$C_2$ = molar ratio

The data show that although 99.9 mol % overall selectivity to ethylbenzene (EB), diethylbenzene (DEB), and triethylbenzene (TEB) was observed for both catalysts, MCM-49 is more selective for the desired EB product. It produced 20% less DEB+TEB than MCM-22. The higher selectivity of MCM-49, presented as DEB/EB molar ratio, at other temperatures is shown in FIG. 2: in liquid phase (<260° C.), MCM-49 is more selective (lower DEB/EB ratio) than MCM-22.

What is claimed is:

1. A process for the production of ethylbenzene, said process comprising alkylating benzene with ethylene under sufficient liquid phase conditions in the presence of a catalyst comprising MCM-49, said MCM-49 having, in as-synthesized form, the X-ray diffraction pattern of Table 1, and said MCM-49 having, in calcined form, the X-ray diffraction pattern of Table 2, wherein the form of the MCM-49 in said catalyst is a calcined, aluminosilicate form.

2. A process according to claim 1, wherein said MCM-49 in said catalyst has a bulk silica:alumina molar ratio of less than about 24:1.

3. A process according to claim 1, wherein said MCM-49 in said catalyst has a bulk silica:alumina molar ratio of less than about 20:1.

4. A process according to claim 1, wherein said liquid phase conditions include a temperature of at least 150° C.

5. A process according to claim 1, wherein said liquid phase conditions include a temperature of from 160° to 320° C.

\* \* \* \* \*